US006773437B2

(12) United States Patent
Ogilvie et al.

(10) Patent No.: US 6,773,437 B2
(45) Date of Patent: Aug. 10, 2004

(54) SHAPE MEMORY ALLOY STAPLE

(75) Inventors: James Ogilvie, Edina, MN (US); Troy D. Drewry, Memphis, TN (US); Michael C. Sherman, Memphis, TN (US); Jean Saurat, Avrill (FR)

(73) Assignee: SDGI Holdings, Inc., Wilmington, DE (US)

( * ) Notice: Subject to any disclaimer, the term of this patent is extended or adjusted under 35 U.S.C. 154(b) by 118 days.

(21) Appl. No.: 09/967,148

(22) Filed: Sep. 28, 2001

(65) Prior Publication Data

US 2002/0019636 A1 Feb. 14, 2002

Related U.S. Application Data

(62) Division of application No. 09/421,903, filed on Oct. 20, 1999, now Pat. No. 6,325,805.
(60) Provisional application No. 60/130,909, filed on Apr. 23, 1999.

(51) Int. Cl.[7] .............................................. A61B 17/84
(52) U.S. Cl. ........................................................ 606/75
(58) Field of Search .............................. 606/61, 72, 75, 606/213, 219–221, 69

(56) References Cited

U.S. PATENT DOCUMENTS

| 4,047,524 A | 9/1977 | Hall |
| 4,170,990 A | 10/1979 | Baumgart et al. |
| 4,263,903 A | 4/1981 | Griggs |

(List continued on next page.)

FOREIGN PATENT DOCUMENTS

| EP | 0 127 994 | 12/1984 | ........... A61B/17/18 |
| EP | 0 545 830 A1 | 6/1993 | |
| FR | 2 603 794 | 3/1988 | ........... A61B/17/58 |
| FR | 2 628 312 | 9/1989 | ........... A61B/17/58 |
| FR | 2 694 696 | 2/1994 | ........... A61L/31/00 |
| FR | 2 743 490 A1 | 7/1997 | ........... A61B/17/58 |
| FR | 2 754 702 | 4/1998 | ........... A61B/17/70 |
| FR | WO98/17189 | * 4/1998 | ......... A61B/17/800 |
| SU | 1152582 A | 4/1985 | |
| WO | WO 92/17122 | 10/1992 | ........... A61B/17/58 |

OTHER PUBLICATIONS

*Treatment of Intra–Articular Fractures with Shape Memory Compression Staples*, K. R. Dai, X. K. Hou, Y. H. Sun, R. G. Tang, S. J. Qiu and C. Ni, Injury, (1993) 24, (IO), 651–655.
*The Use of a Shape Memory Staple in Anterior Cervical Fusion*, Docteur Olivier Ricart.
U.S. patent application Ser. No. 09/421,207, Ogilvie et al., filed Oct. 20, 1999.
U.S. patent application Ser. No. 09/421,976, Drewry et al., filed Oct. 22, 1999.
*The Use of Nickel–Titanium Alloy in Orthopedic Surgery in China*, Kuo, M.D.; Yang, M.D.; Zhang, M.D.; Yang; Yu, M.D.; Dai, M.D.; Hong; Ke, M.D.; Cai, M.D.; Tao, M.D.; Orthopedics, Jan. 1989, vol. 12/No. 1.

(List continued on next page.)

*Primary Examiner*—Kevin Shaver
*Assistant Examiner*—Michael B. Priddy
(74) *Attorney, Agent, or Firm*—Woodard, Emhardt, Moriarty, McNett & Henry LLP

(57) ABSTRACT

A fusionless method of correcting spinal deformities in growing adolescents is disclosed utilizing a shape memory alloy staple. Various embodiments of the shape memory alloy staple include features such as barbs on the inner and outer surfaces of the prongs in the shape memory alloy staple as well as the use of notches on the crossbar or cross plate connecting the prongs to the shape memory alloy staple. In some embodiments, the shape memory alloy staple has an aperture defined through the cross plate for receiving a bone screw or other bone anchor which in turn allows the interconnection of a longitudinal member.

34 Claims, 11 Drawing Sheets

U.S. PATENT DOCUMENTS

| | | | |
|---|---|---|---|
| 4,278,091 A | | 7/1981 | Borzone |
| 4,321,002 A | | 3/1982 | Froehlich |
| 4,434,796 A | | 3/1984 | Karapetian et al. |
| 4,454,875 A | | 6/1984 | Pratt et al. |
| 4,485,816 A | | 12/1984 | Krumme |
| 4,570,623 A | | 2/1986 | Ellison et al. |
| 4,723,540 A | | 2/1988 | Gilmer, Jr. |
| 4,756,711 A | | 7/1988 | Mai et al. |
| 5,002,563 A | | 3/1991 | Pyka et al. |
| 5,046,513 A | | 9/1991 | Gatturna et al. |
| 5,053,038 A | | 10/1991 | Sheehan |
| 5,089,009 A | | 2/1992 | Green |
| 5,108,395 A | | 4/1992 | Laurain |
| 5,190,546 A | | 3/1993 | Jervis |
| 5,209,756 A | | 5/1993 | Seedhom et al. |
| 5,222,975 A | | 6/1993 | Crainich |
| 5,246,443 A | | 9/1993 | Mai |
| 5,304,204 A | | 4/1994 | Bregen |
| 5,324,307 A | | 6/1994 | Jarrett et al. |
| 5,342,396 A | | 8/1994 | Cook |
| 5,352,229 A | | 10/1994 | Goble et al. |
| 5,366,479 A | | 11/1994 | McGarry et al. |
| 5,395,372 A | * | 3/1995 | Holt et al. .................... 606/61 |
| 5,449,359 A | | 9/1995 | Groiso |
| 5,454,814 A | | 10/1995 | Comte |
| 5,474,557 A | | 12/1995 | Mai |
| 5,551,871 A | | 9/1996 | Besselink et al. |
| 5,578,034 A | * | 11/1996 | Estes .......................... 606/61 |
| D378,409 S | | 3/1997 | Michelson |
| 5,645,599 A | | 7/1997 | Samani ....................... 623/17 |
| 5,660,188 A | | 8/1997 | Groiso |
| 5,690,629 A | * | 11/1997 | Asher et al. .................. 606/61 |
| 5,728,127 A | | 3/1998 | Asher et al. .................. 606/61 |
| 5,779,707 A | | 7/1998 | Bertholet et al. ............. 606/75 |
| 5,785,713 A | | 7/1998 | Jobe ............................ 606/69 |
| 5,853,414 A | | 12/1998 | Groiso |
| 5,941,890 A | | 8/1999 | Voegele et al. |
| 6,083,242 A | | 7/2000 | Cook |
| 6,336,928 B1 | * | 1/2002 | Guerin et al. ................. 606/61 |

OTHER PUBLICATIONS

*Nickel–titanium Osteosynthesis Clips*, Bensmann, Baumgart, Haasters, Reprint from *Medical Focus*, 1983.

*Application of a NiTi Staple in the Metatarsal Osteotomy*, Tang, Dai, Chen, *Bio–Medical Materials and Engineering 6*, (1996) 307–312, IOS Press.

*Applications of Shape Memory Effects*, Besselink, Sachdeva, Memory Metal Holland, *Memory Medical Systems*, Publication date unknown.

*The Use of a Memory Shape Staple in Cervical Anterior Fusion*, Ricart, *Proceedings of the Second International Conference on Shape Memory and Superelastic Technoloiges*, Asilomar Conference Center, Pacific Grove, CA, USA, 1997.

*The Use of a Shape Memory Staple in Anterior Cervical Fusion*, Ricart, Publication date unknown.

Publication entitled "The Use of Ni–Ti as an Implant Material in Orthopedics", by Dr. J. Haasters, Prof. G. v.Salis–Solio, & Dr. G. Bensmann, pp. 426–444.

Publication entitled "Medical Applications of Ni–Ti Alloys in China", by Shibi Lu, M.D., pp. 445–451.

* cited by examiner

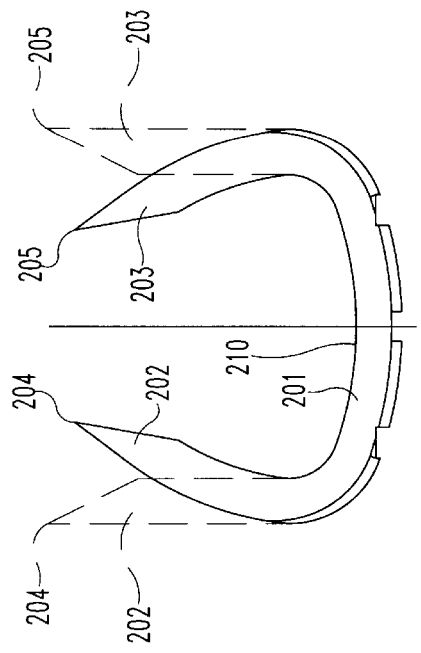
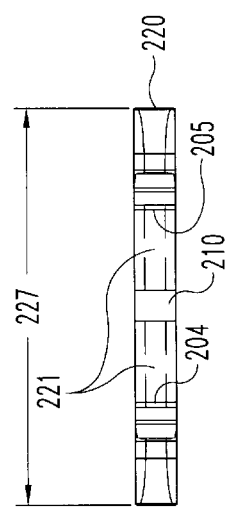
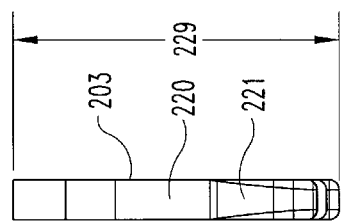
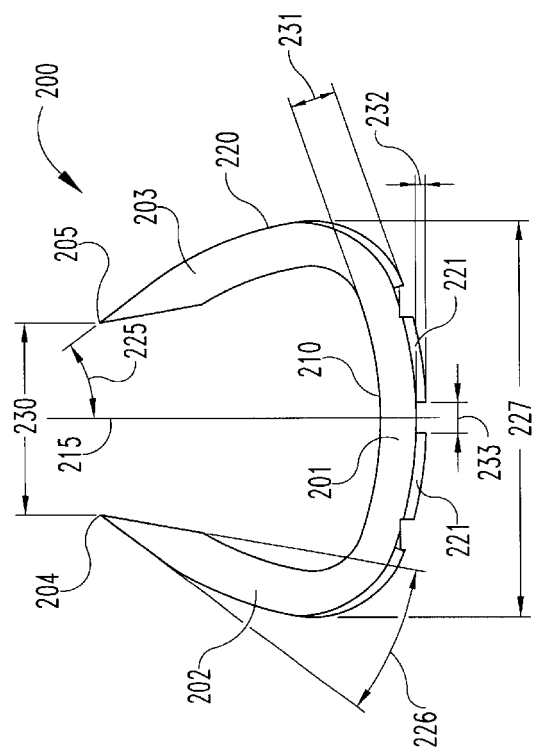
Fig. 3D
Fig. 3C
Fig. 3B
Fig. 3A

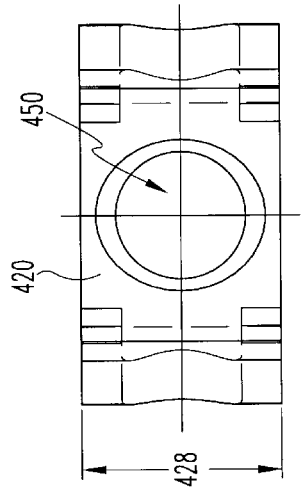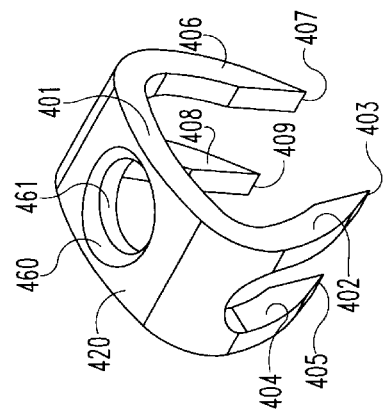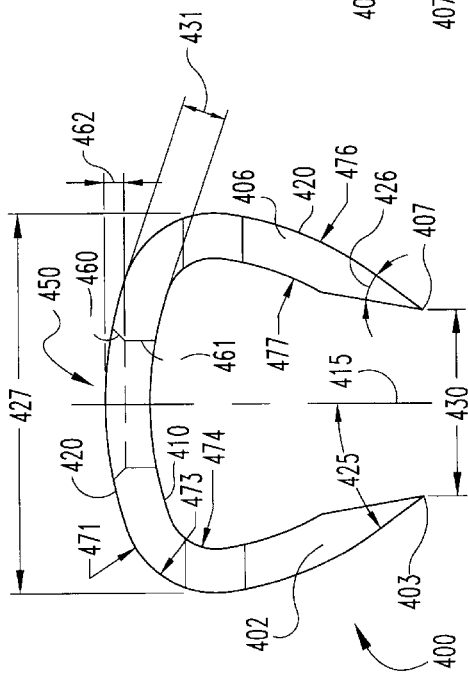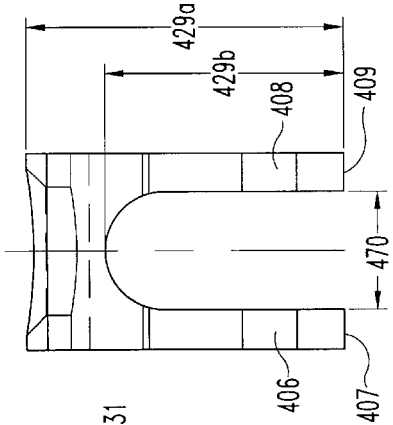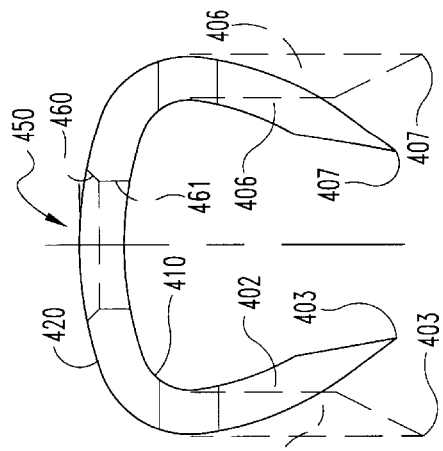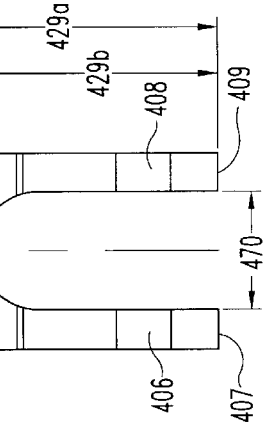

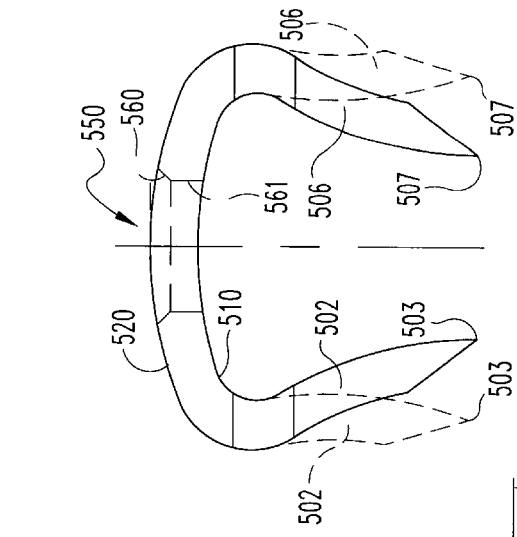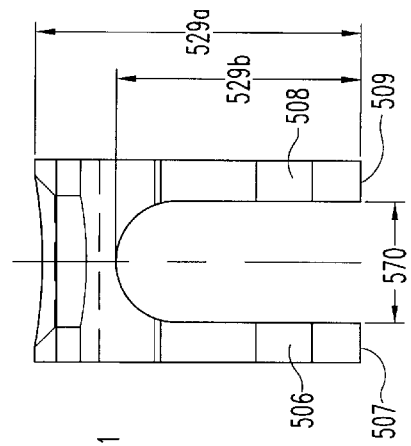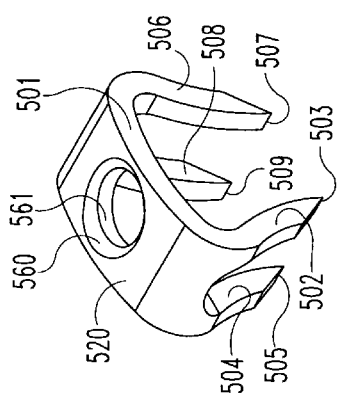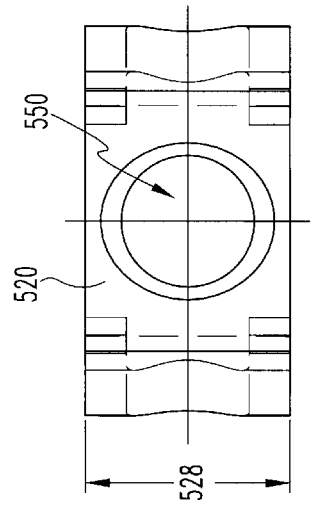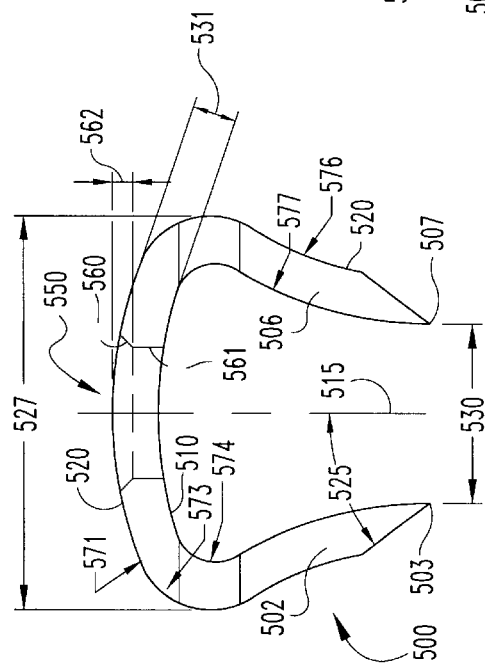

SHAPE MEMORY ALLOY STAPLE

The present Application is a divisional of U.S. patent application Ser. No. 09/421,903, filed Oct. 20, 1999 now U.S. Pat. No. 6,325,805, which claims benefit of U.S. Provisional Application No. 60/130,909, filed Apr. 23, 1999, the contents of each application hereby being incorporated by reference.

BACKGROUND OF THE INVENTION

Current operative methods for treating spinal deformities, particularly scoliosis, include correction of the curve by some internal fixation device, and fusion of the spine in the corrected state usually accomplished by the placement of bone graft between vertebrae. This is usually accomplished with posterior surgery, although anterior procedures are becoming more popular, as well as combinations of anterior and posterior procedures. Several instrumentation systems are available from various manufacturers to correct and stabilize the spine while fusion occurs. Among them are TSRH®, CD™, CD Hopf™, CD Horizon™, ISOLA™, Moss Miami and Synthes Universal Spine Systems. Nonoperative methods do exist and are used when applicable. These nonoperative methods include bracing and observation.

Juvenile idiopathic scoliosis occurs between the ages of 4 and 10 years. It can resolve spontaneously, respond to nonoperative therapy, or progress until fusion is required. Stapling across long bone physes has long been recognized as a predictable method of treating limb malalignment. Vertebral interbody stapling across the cartilaginous endplates and discs was attempted by Nachlas and Borden in a canine scoliosis model. Early human results in the 1950s were disappointing. Roaf reported limited successful correction of scoliosis by uninstrumented convex hemiepiphysiodesis. His study did not have a uniform patient population by skeletal maturity or scoliosis etiology.

Further shortcomings of current operative methods and devices are numerous. Patients with juvenile scoliosis who undergo curve stabilization with subcutaneous rods would be subject to multiple surgical procedures for lengthening as they grow. Anterior and/or posterior spinal fusion in the skeletally immature patient often results in loss of vertebral body height and girth. Additionally, poor self-image may occur in adolescent patients who are braced for scoliosis. Moreover, curve stabilization with bracing is only successful in approximately 75% of patients. Another problem is that some children, while not currently candidates for a definitive fusion procedure, are likely to need such a procedure in the future. These would include children less than ten years of age, small in stature, premenstrual or riser two or lower, and those not physically able to tolerate the surgery required for a definitive fusion procedure. It would be preferable to eliminate the need for that procedure altogether.

SUMMARY OF THE INVENTION

In one embodiment, the staple comprises a plate having a first end and a second end and a top surface and a bottom surface and first and second side surfaces, the surfaces extending between the first end and the second end. The plate defines a bore therethrough between the top surface and the bottom surface with a first pair of prongs connected to the first end. Each of the first pair of prongs has a lower end with a tip and an upper end connected to the first side surface. Additionally, each of the first pair of prongs has an interior surface and an exterior surface extending between the lower end and the upper end. The interior surface and the exterior surface of the upper end of the first pair of prongs are adjacent the bottom surface and the top surface respectively of the plate. A second pair of prongs is connected to the second end, each of the second pair of prongs has a lower end with a tip and an upper end connected to the second side surface. Also, each of the second pair of prongs has an interior surface and an exterior surface extending between the lower end and the upper end. The interior surface and the exterior surface of the upper end of the second pair of prongs is adjacent the bottom surface and the top surface respectively of the plate. At least a portion of the staple is manufactured from a shape memory material. The shape memory material has a first memorized state and a second deformed state. The tips of the first pair of prongs are closer to the tips of the second pair of prongs in the first state than in the second state.

In another embodiment, the staple comprises a bridging portion with a first end and a second end and an upper surface and a lower surface and first and second side surfaces, the surfaces extending between the first end and the second end. The staple has a first prong having a first proximal end and a first distal end, the first prong also has a first inboard surface and a first outboard surface extending between the first proximal end and the first distal end. The staple also has a second prong having a second proximal end and a second distal end, the second prong having a second inboard surface and a second outboard surface extending between the second proximal end and the second distal end. A plurality of notches are integrally formed on the upper surface of the bridging portion, the notches permit more precise seating of the staple. The first proximal end is connected to the first end of the bridging portion, and the second proximal end is connected to the second end of the bridging portion. The first and second inboard surface generally face one another. Additionally, at least a portion of the staple is made from a shape memory material. The shape memory material has a first memorized state and a second deformed state. The first distal end is closer to the second distal end in the first state than in the second state.

In another embodiment, the staple is generally U-shaped with a cross bar defining a central axis extending between a first end and a second end. The staple has a first leg with a first proximal portion and a first distal portion. The first proximal portion is integrally formed with the first end. The first leg defines a first longitudinal axis and the first longitudinal axis is at an angle to the central axis. The staple also has a second leg with a second proximal portion and a second distal portion. The second proximal portion is integrally formed with the second end. The second leg defines a second longitudinal axis with the second longitudinal axis being at an angle to the central axis. The cross bar and the first and second legs each have an inner surface and an outer surface and a pair of side surfaces with the inner surfaces of the first and second legs generally facing one another. Additionally, inner and outer surfaces of the first and second legs each contain a plurality of barbs in a direction transverse to the direction of the first and second longitudinal axis respectively.

BRIEF DESCRIPTION OF THE DRAWINGS

FIG. 3A is a side view of another embodiment of a spinal staple.

FIG. 3B is a top view of the spinal staple of FIG. 3A.

FIG. 3C is a side view of FIG. 3A.

FIG. 3D is a side view of the embodiment of the spinal staple of FIG. 3A with the insertion position shown in phantom.

FIG. 5A is a side view of another embodiment of a spinal staple of the present invention.

FIG. 5B is a top view of the embodiment of FIG. 5A.

FIG. 5C is another side view of the embodiment of the spinal staple of FIG. 5A.

FIG. 5D is a perspective view of the embodiment of FIG. 5A.

FIG. 5E is a side view of the embodiment of the spinal staple of FIG. 5A showing the tines in the insertion position in phantom.

FIG. 6A is a side view of another embodiment of a spinal staple of the present invention.

FIG. 6B is a top view of the embodiment of FIG. 6A.

FIG. 6C is another side view of the embodiment of the spinal staple of FIG. 6A.

FIG. 6D is a perspective view of the embodiment of FIG. 6A.

FIG. 6E is a side view of the embodiment of the spinal staple of FIG. 6A showing the tines in the insertion position in phantom.

DESCRIPTION OF THE PREFERRED EMBODIMENT

Figure 1A:
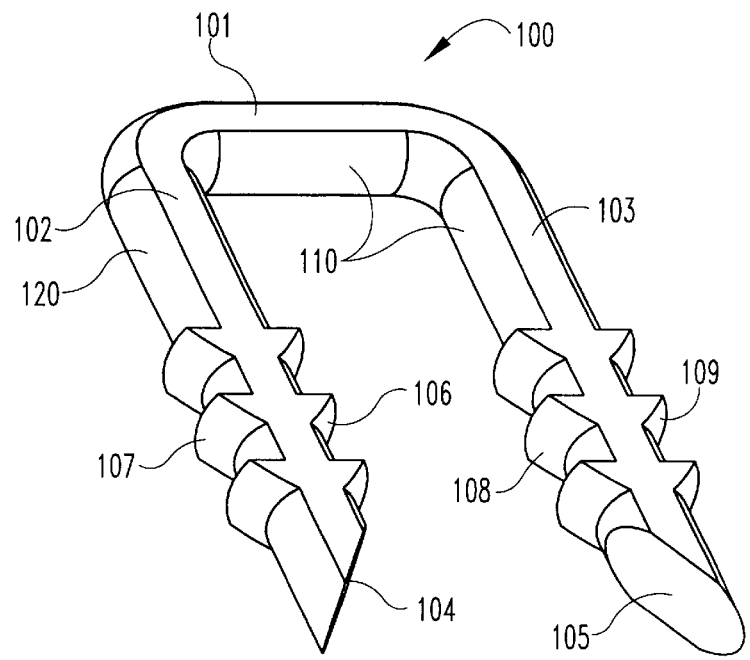
FIG. 1A is a perspective view of an embodiment of a spinal staple in accordance with this invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Various devices and surgical approaches are possible to implement correction of spinal deformities, particularly scoliosis, through fusionless tethering. The correction of the deformity may be achieved by attaching a tether to the vertebral bodies on the convex side of the spine. This tether will minimize or arrest growth on the convex or "long" side of the spine and allow the concave or "short" side of the spine to grow and catch up with the long side. Alternatively, fusionless tethering may treat abnormal spinal alignment by simply preventing further misalignment such as curve progression.

A wide variety of surgical approaches may be used in implementing tethering of the convex side. One approach is an open thoracotomy (standard). Another surgical approach contemplated is a minimally invasive thoracoscopic approach (endoscopic). The surgical approach may also be a combined anterior/posterior approach (standard or endoscopic). It should be understood that tethering can be practiced using other surgical approaches known to persons of ordinary skill in the art.

In any surgical approach used in tethering, the tether used to selectively constrain growth will include at least one longitudinal element and one anchor with an interconnection between the longitudinal element and the anchor. In some cases the longitudinal element and the anchor may be one and the same. The following discusses generally some of the types of apparatus that may be used. Additionally, it should be understood that most, if not all, of the longitudinal elements or anchors may be manufactured from, but are not limited to, conventional implant metals, such as stainless steel or titanium. It should be further understood, and will be discussed in some detail for particular embodiments, that the longitudinal elements and anchors may take advantage of the shape memory and superelastic characteristics of shape memory materials including, for example, a shape memory alloy ("SMA") such as nickel titanium.

Several devices are contemplated for spanning the longitudinal aspect of the spine during the fusionless tethering procedure. A list of potential longitudinal elements includes, but is not limited to, staples, cables, artificial strands, rods, plates, springs, and combinations of devices from the foregoing list. Details of each individual element will be discussed briefly.

The longitudinal element may be a spinal staple formed in a variety of shapes and sizes depending on its application. Staples may act as either the longitudinal element, the anchor, or both. These staples may be manufactured from conventional implant metal, such as stainless steel or titanium. In one preferred embodiment, however, the staples are manufactured out of shape memory materials or alloys such as nickel titanium to enhance fixation. One example of such an alloy is Nitinol sold by Memry Corporation of Menlo Park, Calif. Further details of preferred use, size, and material selection for the spinal staple are discussed further below.

Another possible selection for the longitudinal element is cabling. Historical spinal instrumentation involved the use of cables (Dwyer) as a fixation method for spinal fusion. However, this use of cable never contemplated that a flexible cable could represent the longitudinal element in a fusionless tethering procedure.

The use of artificial or synthetic strands, much in the same way cable could be used, may potentially add additional flexibility and motion to this fusionless tethering procedure. In one preferred embodiment the artificial strand may be manufactured from a braided polymer rope. In another preferred embodiment the artificial strand will be an adjustable spinal tether. Details of various embodiments of the adjustable spinal tether may be found in provisional patent application U.S. Ser. No. 60/130,910, entitled "Adjustable Spinal Tether" filed on Apr. 23, 1999 and commonly assigned to the assignee of the present application, the disclosure of which is incorporated herein by reference. Such an artificial strand is preferably (but not necessarily) used in conjunction with a block similar or identical to various embodiments of the "Hopf blocks" disclosed in U.S. Pat. No. 5,702,395 to Hopf entitled "Spine Osteosynthesis Instrumentation for an Anterior Approach" the disclosure of which is incorporated herein by reference. It is contemplated as within the scope of the invention, however, that the artificial strand may be utilized for fusionless tethering in a variety of manners. These include, but are not limited to, being attached to or around anchors such as screws and staples. It is further contemplated as within the scope of the invention that the artificial strand may also act as both the longitudinal element and the anchor by being secured directly around the vertebrae to be tethered.

Another possible selection for the longitudinal element is a flexible rod. These could be manufactured of small diameter and/or flexible material such as a super elastic SMA. In a similar manner plates may be used as a longitudinal element. The plates can be used with or without slots allowing implants to slide. Another possible choice is a spring. Springs have been used historically in spinal instrumentation and could form the longitudinal element. Again, to reiterate, it should be understood that combinations of any or all of the above may be used as a longitudinal element when deemed appropriate.

Most of the longitudinal elements discussed above, the staples and artificial strands being possible exceptions, will need to be anchored to the vertebral bodies in order to effectively tether them. Several different anchors are contemplated.

As previously mentioned, staples can be both anchors as well as longitudinal elements since they possess the characteristics of both. These staples can be either conventional or a SMA as stated above. Also available for use in this capacity are scaled up suture anchor type products. Novel approaches using such products known in the art are available to fix to soft cancellous bone such as that found in a vertebral body. Additionally, screw down fixation plates, posts, etc. as are known to those of ordinary skill in the art, may be used as anchors.

Another potential anchor is an expandable screw. Examples include Mollie bolt type implants that are initially screwed into the vertebral body and expand through some mechanism. It is again possible to take advantage of the properties of shape memory materials to accomplish the expansion mechanism. Conventional screws and bone screws may also serve as anchors. These screws may be coated with any number of osteoinductive or osteoconductive materials to enhance fixation as desired. Also, a variety of screws used in combination with certain embodiments of spinal staples are discussed in further detail below.

The selection of the longitudinal elements and anchors from those previously discussed and others known in the art also leaves possible the selection of a wide variety of interconnections between the two. Once the anchors are in place, their connection to the longitudinal elements can be governed by a number of different parameters. They could be constrained or unconstrained connections; the anchor could be allowed to slide along the longitudinal element or articulate with it, as in the case of a ball joint, or even float within some neutral zone. Several scenarios are envisioned.

The first is constrained. This would involve constrained interconnection scenarios between all anchors and longitudinal elements. The second is un-constrained. This would involve simple connections in which no significant restrictions exist between the longitudinal element and the anchor. An example is an artificial strand band around a post, or a screw through an artificial strand ribbon.

The third scenario is ends constrained with middle elements un-constrained. In this case the construct would possess constrained interconnections between the end anchors and the longitudinal elements with unconstrained interconnections in between. These unconstrained interconnections could be either sliding situations or ball joint situations. The fourth scenario is ball joint interconnections. Ball joints represent a semi-constrained situation in which the anchor cannot slide up or down the longitudinal element, but can articulate within some spherical range of motion. It should be understood that combinations of any or all of the above may be used as appropriate in practicing fusionless tethering.

The above disclosure deals specifically with the broad range of device concepts envisioned for fusionless tethering of deformities in order to achieve permanent correction. The specifics with regard to the method of practicing fusionless tethering are similarly broad. A wide range of spinal deformities could be managed. The primary indications will be progressive idiopathic scoliosis with or without sagittal deformity in either infantile or juvenile patients. The preferred patient population upon which to practice the present invention is prepubescent children (before growth spurt) less than ten years old. Other patient groups upon which the present invention may be practiced include adolescents from 10–12 years old with continued growth potential. It should be understood that fusionless tethering may be used on older children whose growth spurt is late or who otherwise retain growth potential. It should be further understood that fusionless tethering may also find use in preventing or minimizing curve progression in individuals of various ages.

Generally, in the case of scoliosis, tethering will take place on the convex side of the curve. An anterior, minimally invasive (thoracoscopic) procedure can be carried out on the convex side of the spinal curve in order to prevent continued growth on that side of the curve. As the pre-growth spurt child approaches puberty, the untethered side of the spine will grow unconstrained, ultimately eliminating the curvature of the spine in the frontal plane. It is preferable to deliver this method of treatment in a minimally invasive approach using thoracoscopic instrumentation. It is contemplated as within the scope of the invention, however, that open use of these systems may be appropriate in some cases. It is further contemplated as within the scope of the invention that the procedure may be posterior as well as anterior, or some combination of both. Finally, it should be understood that if the procedure fails to correct the curve but does, in fact, prevent further progression (which includes increase in the magnitude of the curve) it can and should be considered successful.

In one embodiment, fusionless correction of scoliosis is achieved by thoracoscopically placing shape memory alloy staples into the vertebral bodies on the convex side of the spine. The staples will span the intervertebral space and act as a tether on the spine. This tether will arrest growth on the convex ("long") side of the spine and allow the concave ("short") side of the spine to grow and catch up with the long side. Once correction is achieved, the staple may then be removed thoracoscopically if desired. The removal of the staples permits further growth of the vertebral bodies. It should be understood that the method described is equally applicable in non-endoscopic procedures. It should be further understood that the staples used may be made of a conventional implant metal such as titanium or stainless steel instead of a SMA.

The following contraindications for use of thoracoscopically assisted spinal stapling should be noted: (1) Inability to wear an orthosis postoperatively, (2) Greater than 40 degree kyphosis, (3) Medical contraindication to general anesthetic, (4) Pulmonary function which would contraindicate intraoperative collapse of the convex lung, and (5) Scoliosis deformity where three or more disc spaces are not accessible to thoracoscopically assisted vertebral interbody stapling. It should be understood, however, that the presence of any or all of the above mentioned contraindications does not preclude the potential utility of spinal stapling and/or vertebral body tethering.

The general details of one embodiment of the surgical technique would be as follows. General anesthesia is utilized. A double lumen endotracheal tube is inserted, with possible assistance of fiberoptic visualization. The convex lung is collapsed. A general or vascular surgeon familiar with endoscopic surgery in the thorax may be used as an assistant. The patient is positioned in the lateral decubitus position with the convex side of the scoliosis in the up position. The table is not flexed. Five vertebrae (four intervertebral discs) are usually stapled. The apical vertebral body, the two vertebrae proximal, and the two vertebrae distal are treated. Three endoscopic ports are utilized. The first port is anterior and positioned over the apex of the scoliosis. The second and third ports are made in the posterior auxiliary line with the second port being centered over the second vertebrae of the five being treated and the third port being centered over the fourth vertebrae being treated. The endoscope is maintained in the first port and a fan retractor is placed in the second port. An anterior-posterior (AP) radiograph is used to confirm the levels. The parietal pleura is not excised and the segmental vessels are avoided.

A number of general surgical instruments are used in the procedure along with the following system specific implants and instruments. The main implant is of course a spinal staple, preferably manufactured from a shape memory material. The size will vary depending on the size and number of the vertebral bodies to be spanned. The instruments used in the procedure may also include: Staple Awl, Staple Opener, Straight Staple Inserter, Angled Staple Inserter, Staple Impactor, Staple Extractor.

Pilot holes are made using the Staple Awl. The pilot holes are made anterior to the midbody of the vertebrae. The Staple Awl is inserted part way and position is checked with either x-ray or image intensifier. Prior to removal of the Staple Awl from the pilot holes, an electric cauterizer (Bovie) can be placed in contact with the endcap of the Staple Awl to minimize bleeding from the pilot holes. In one preferred embodiment, two sets of pilot holes are made at each level to accommodate two staples per disc space. Two staples are then placed spanning each disc space. The first staple is loaded into either the Straight Staple Inserter or the Angled Staple Inserter. The staple is then placed into the pilot holes previously made with the Staple Awl. The Inserter may be tapped with a mallet to facilitate placement of the staple. The staple is then released from the Inserter and then the instrument is removed. If further seating of the staple is required, the Staple Impactor may be used in conjunction with a mallet for final seating of the staple into the bone. The aforementioned steps are repeated for the next staple at that spinal level. It should be understood, however, that tethering may also be accomplished with just one staple instead of two spanning each disc space. It should be further understood that the use of more than one staple allows for correction of spinal curvature in more than one plane.

The instruments in the second and third ports are switched and the remaining two discs are stapled. The wounds are closed and a ten or twelve gauge chest tube is inserted which is withdrawn at twenty-four hours postop. The chest tube is used to prevent pneumothorax since there is no hemothorax. Once the endoscope is in place, the remainder of the procedure seldom takes more than one hour. Hospitalization is usually for two to three days.

Apical vertebral interbody stapling theoretically affords immediate and reversible fixation of the anterior vertebral physes. Thoracoscopic insertion minimizes damage to surrounding tissues and permits placement of multiple staples to allow curve correction in more than one plane.

Figure 1B:
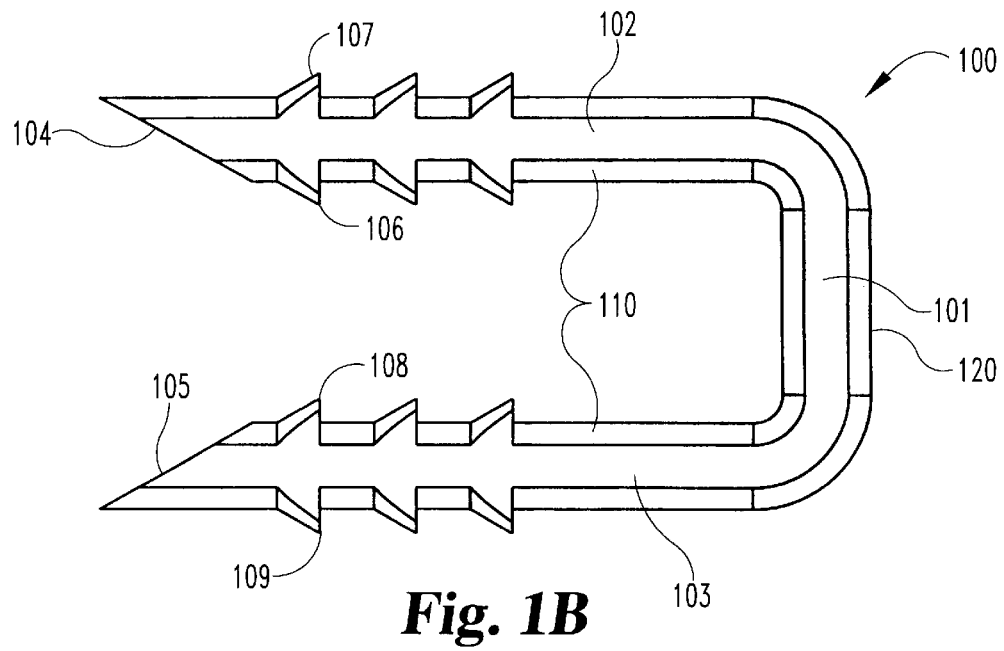
FIG. 1B is a side view of the spinal staple of FIG. 1.

With reference to FIGS. 1A and 1B, one embodiment of an vertebral interbody staple 100 that may be used in the above described method is shown. Staple 100 is generally U-shaped with crossbar 101 between legs 102 and 103. Staple 100 has inner surface 110 and outer surface 120. Leg 102 has a pointed tip 104 and leg 103 has a pointed tip 105 for insertion into the vertebral bodies. It should be understood that tips 104, 105 may have a variety of configurations. Leg 102 has barbs 106 on inner surface 110 and barbs 107 on outer surface 120. Similarly, leg 103 has barbs 108 on inner surface 110 and barbs 109 on outer surface 120. Barbs 106, 107, 108, and 109 aid in the prevention of staple backout. Having barbs on both inner surface 110 and outer surface 120 of each leg 102, 103 of staple 100 allows the use of shorter barbs in the direction transverse to the longitudinal axis of each leg. It should be understood, however, that each leg 102, 103 may only have barbs on the inner surface 110 or outer surface 120.

It should be noted that in one preferred embodiment crossbar 101, and legs 102 and 103 all have a nearly elliptical profile obtained by truncating a circular cross-section. A staple design with an elliptical or near elliptical crossbar 101 is helpful in controlling rotation of the staple 100 and permits some assistance in staple removal. It should be understood that the profile of legs 102, 103 and crossbar 101 may be other than elliptical, such as a circular cross-section. It should be further understood that legs 102, 103 and connecting portion 101 may have different profiles. The staple design of FIGS. 1 and 2 may be made of commercially pure titanium, some other conventional implant metal, or even a SMA.

While details of several embodiments of the staple are discussed in greater detail below, some general points are reviewed here for convenience. The staples are preferably made of nitinol, a biocompatible, shape memory metal alloy of titanium and nickel. Staples are capable of being bent when cooled and reform to their original shape when reheated. It is also possible to take advantage of the shape memory alloy's ability to transform from its austentic state to a stress induced martensitic state. The metal changes shape with temperature or under the influence of stress because of crystalline phase changes. Thus a staple made of a SMA can be inserted in two different ways as desired. In one embodiment the SMA staple is cooled and then deformed while at a temperature less than the transformation temperature at which it is in the martensitic phase. The staple is then inserted in its deformed shape and when heated will reform to its original shape. In a second embodiment the staple is deformed and inserted while held in the deformed state. In the second embodiment the SMA is selected to have a temperature transformation range such that the staple undergoes a transition from austenite to stress-induced martensite under the influence of the deformation forces. Thus, when the staple of the second embodiment is inserted and released it is already at a temperature such that it automatically attempts to reform to its original shape.

The metal's properties at the higher temperature (austenite phase) are similar to those of titanium. The temperature at which the staples will undergo the shape transformation can be controlled by the manufacturing process and the selection of the appropriate alloy composition. Injury to the surrounding tissues should be negligible if the transformation temperature is near body temperature. There is no threat of thermal injury to the spinal cord or nerves, or adjacent vascular structures. Nitinol has a very low corrosion rate and has been used in a variety of medical implants (i.e., orthodontic appliances stents). Implant studies in animals have shown minimal elevations of nickel in the tissues in contact with the metal; the levels of titanium are comparable to the lowest levels found in tissues near titanium hip prostheses.

Figure 2A:
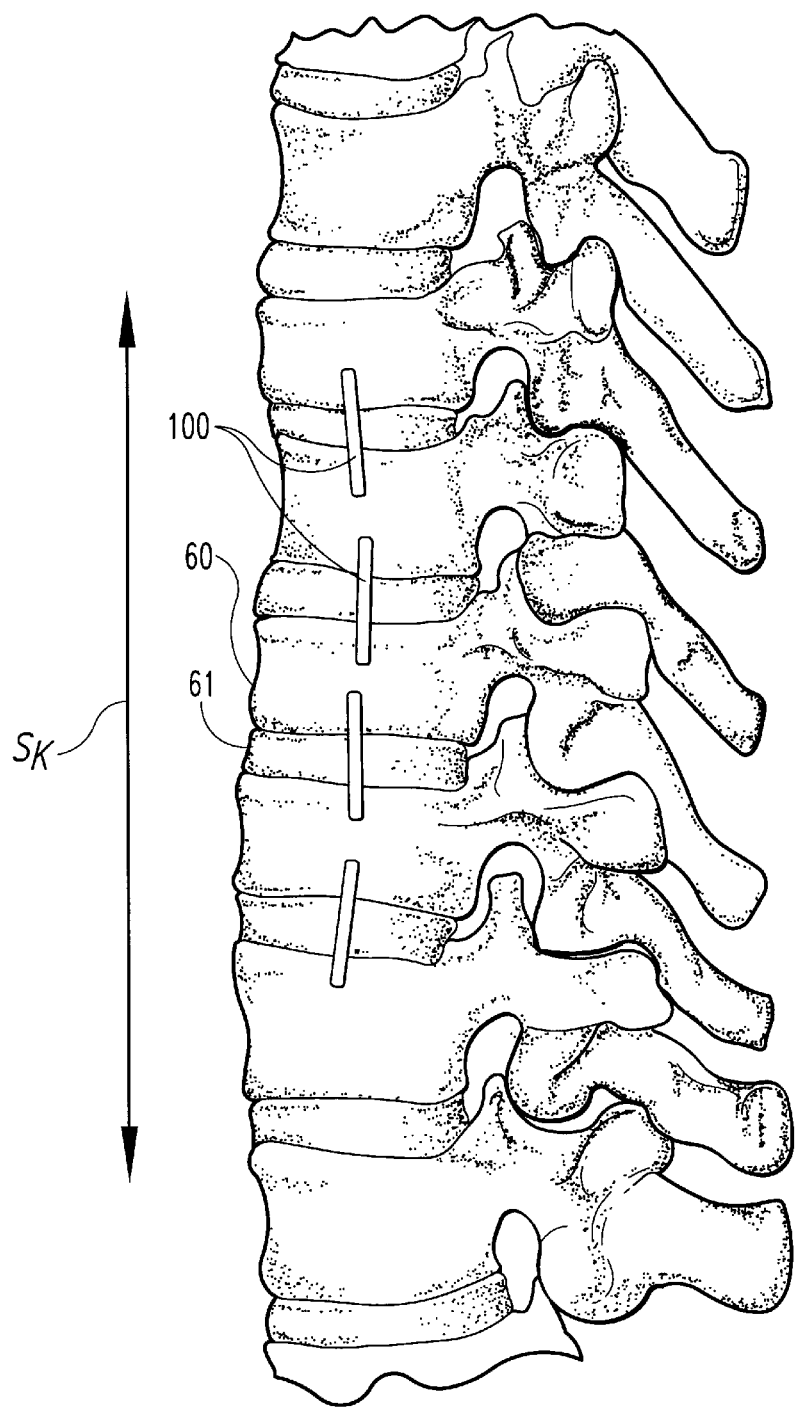
FIG. 2A is a schematic illustration of the embodiment of FIG. 1 attached to vertebral bodies on the convex side of a spine.
Figure 2B:
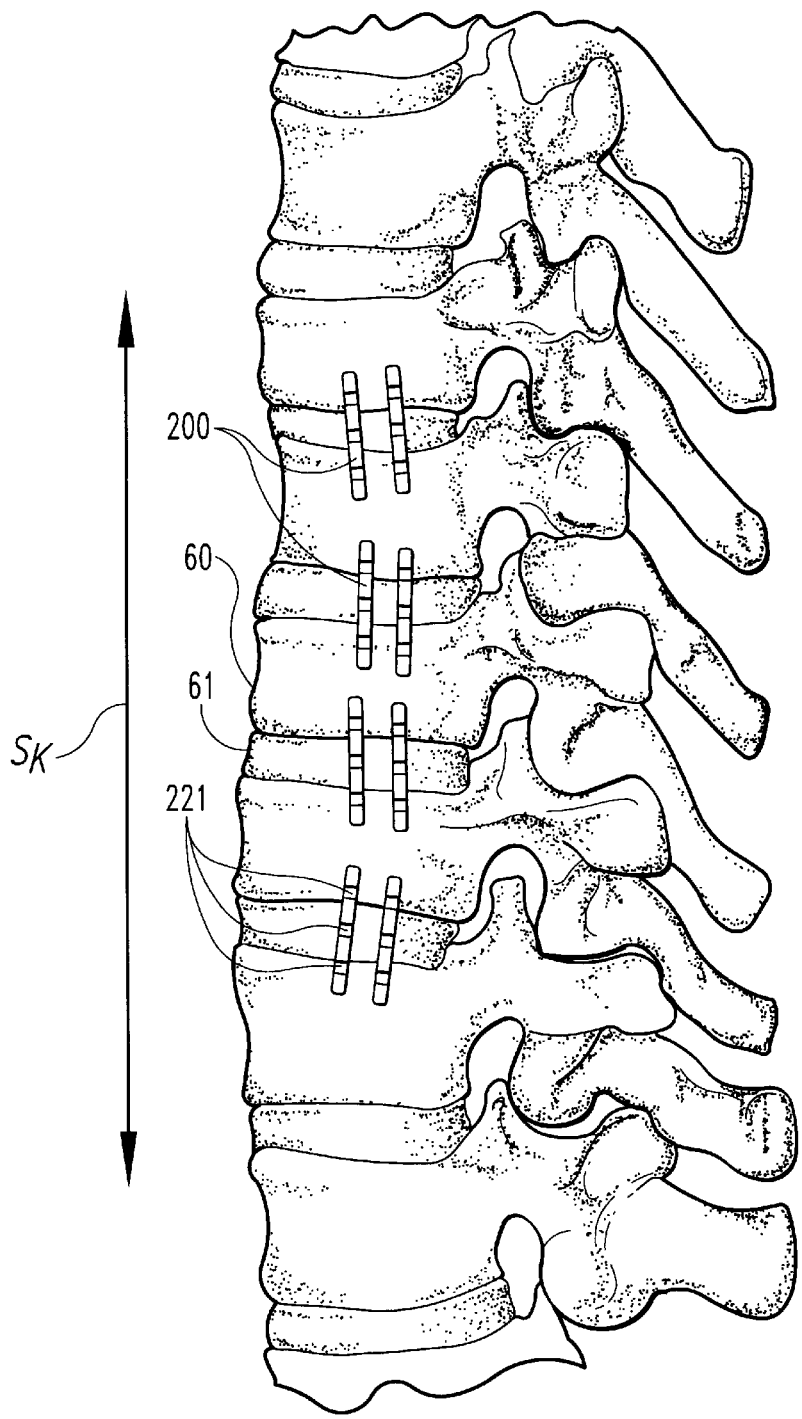
FIG. 2B is a schematic illustration of the embodiment of FIG. 3 or FIG. 4 attached to vertebral bodies on a convex side of a spine.
Figure 2C:
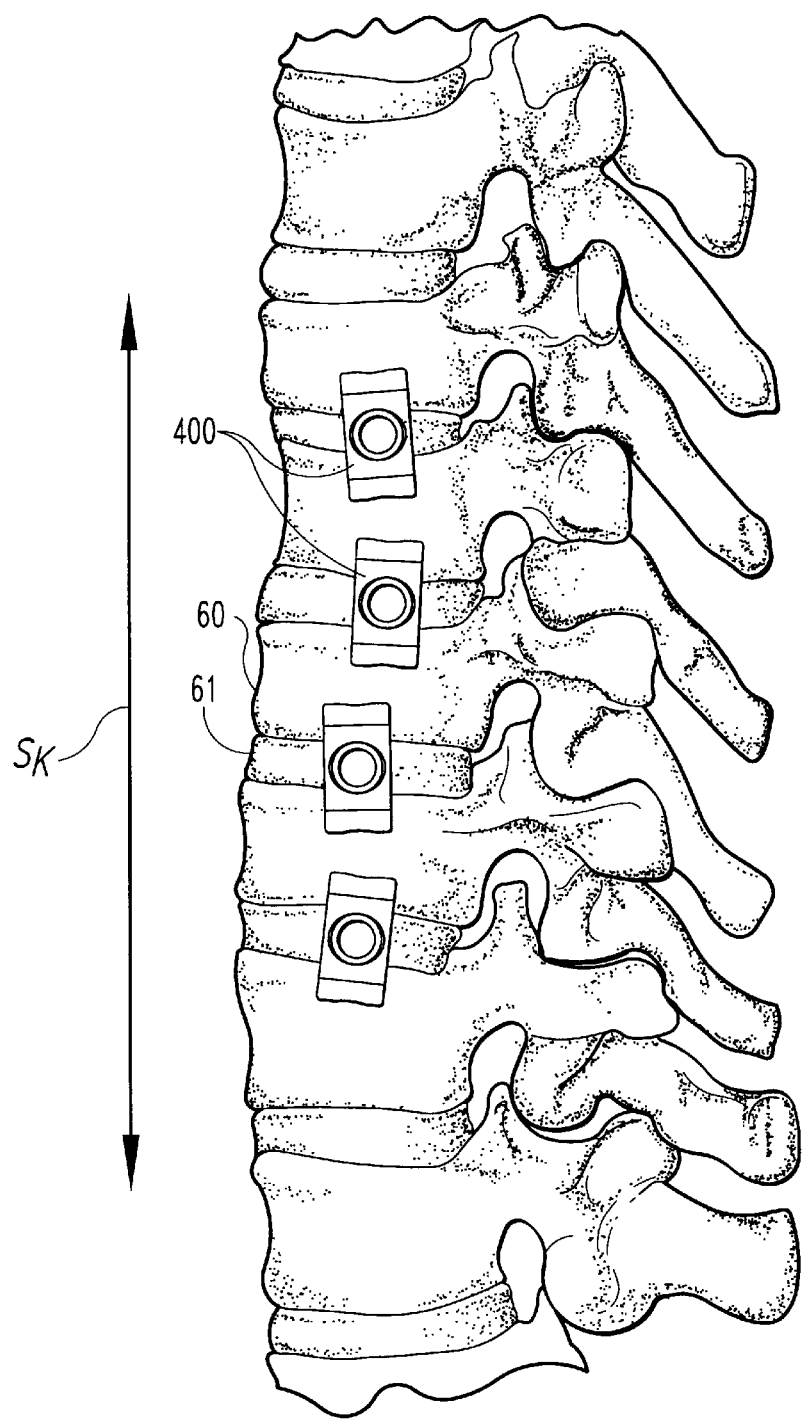
FIG. 2C is a schematic illustration of the embodiment of FIG. 5 attached to vertebral bodies on the convex side of the spine.
Figure 4D:
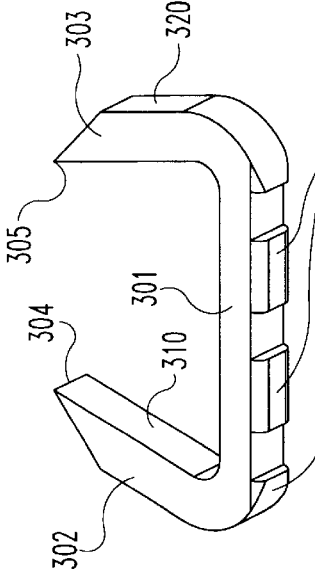
FIG. 4D is a perspective view of the embodiment of the spinal staple of FIG. 4A.
Figure 4E:
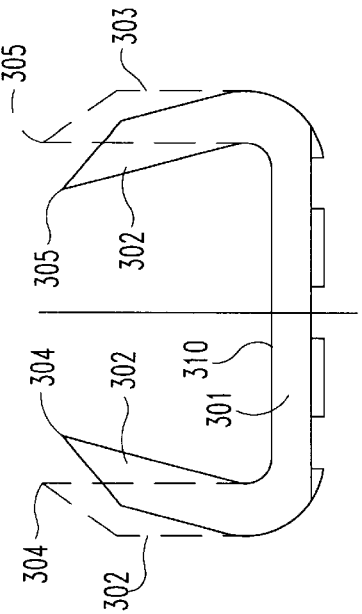
FIG. 4E is a side view of the embodiment of the spinal staple of FIG. 4A showing the tines in the insertion position in phantom.
Figure 4C:
FIG. 4C is a side view of the embodiment of FIG. 4A.
Figure 4B:
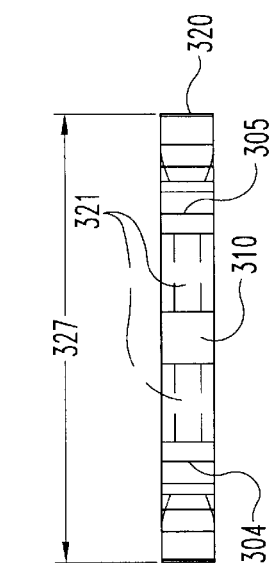
FIG. 4B is a top view of the embodiment of FIG. 4A.
Figure 4A:
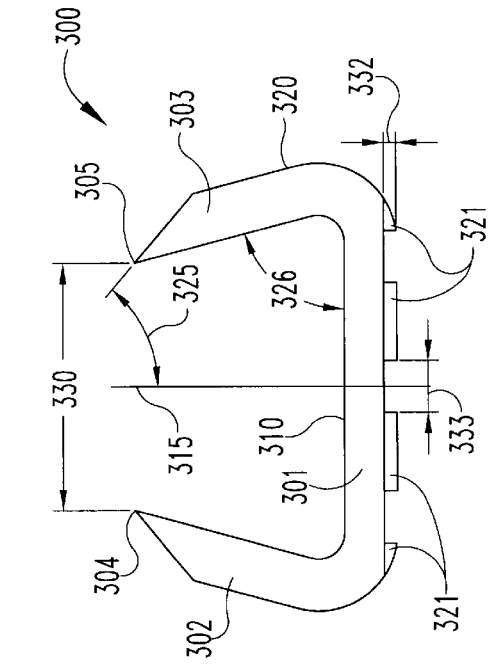
FIG. 4A is a side view of another embodiment of a spinal staple.

With reference to FIGS. 2A–2C there is illustrated various embodiments of spinal staples spanning intervertebral disc 61 and anchored in adjacent vertebra 60. With reference to FIG. 2A, a plurality of spinal staples 100 with legs 102, 103 anchored in adjacent vertebral bodies 60 are shown. Crossbar 101 spans intervertebral disc 61. With reference to FIG. 2B, an embodiment is shown wherein two staples 200 (see FIGS. 3A–3D) are anchored in adjacent vertebral bodies 60. In this embodiment, the spinal staples 200 have notches 221 on the back of the staple for final seating of the staple into bone. This allows the surgeon to drive in each tine independently as necessary. It should be understood that while FIG. 2B illustrates the use of staples 200, these staples may instead be other embodiments such as staples 300 (see FIGS. 4A–4E). With reference to FIG. 2C, a plurality of spinal staples 400 (see FIGS. 5A–5E) are anchored adjacent vertebral body 60. In this embodiment, each spinal staple 400 has four prongs. Again, it should be understood that while FIG. 2C illustrates the use of staples 400, these staples may also be replaced by another embodiment such as staple 500 (see FIGS. 6A–6E). It should be understood that in each of the embodiments of FIGS. 2A–2C the spinal staples may include notches on the back of the staple as desired. It should also be understood that a wide variety of configurations and spacing for the notches in all of the spinal staple embodiments discussed below are contemplated as within the scope of the invention. It should be further understood that any of the embodiments disclosed may entail the use of one, two, or even more than two spinal staples at each level.

With reference to FIGS. 3A–3D, another embodiment of a spinal staple 200, such as that used in FIG. 2B is shown. Vertebral interbody staple 200 is generally U-shaped with cross bar 201 between legs 202 and 203. Staple 200 has inner surface 210 and outer surface 220. Leg 202 has a pointed tip 204 and leg 203 has a pointed tip 205 for insertion into the vertebral bodies. It should be understood that tips 204, 205 may have a variety of configurations. It should be further understood that the legs or tines in all of the embodiments in FIGS. 3–6 may have barbs on the inner surface or outer surface as desired. Similarly, it should be further understood that all of the embodiments of the staples in FIGS. 3–6 may be used in the previously described method of vertebral body tethering without fusion. The back of staple 200 has a plurality of notches 221 for final seating of the staple into the bone or vertebrae. Notches 221 aid the surgeon in driving in each tine or leg 202, 203 independently for more precise seating of staple 200 as necessary (see FIG. 2B).

It should be understood that a variety of sizes, shapes, and configurations of notches are contemplated as within the scope of the invention. The notches find applicability in most, if not all, of the embodiments of a spinal staple disclosed in the present application. As discussed above, the notches aid the surgeon in driving in each tine or prong or leg independently of others to some degree or another. The ability to more carefully direct the implantation of particular tines or prongs or legs allows more precise seating of the staple. The notches may be spaced apart differently for different applications (such as may be the case for an intrabody versus interbody application). Additionally, it should be understood that the surface of each notch may assume a different angle with respect to the staple than other notches or that they may have the same angle. An angled notch surface may permit ease of surgical implantation as the surfaces may be angled so that all can be easily impacted thorascopically or through other minimally invasive surgical techniques which permit smaller incisions and less scarring.

To better illustrate the construction of the staple 200 (see FIGS. 3A–3D), the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. Spinal staple 200 has a center line 215 around which it is symmetrical. An angle 225 subtended by axis 215 and a line extending from the tip 205 of leg 203 preferably defines an angle of 37 degrees plus or minus 5 degrees. Similarly, the angle 226 from between the inner surface 210 and outer surface 220 of leg 202 is preferably 27 degrees plus or minus 5 degrees. The width 230 of the staple 200 between tip 204 and tip 205 is preferably 9.5 mm plus or minus 0.3 mm and the greatest width 227 of staple 200 is preferably 19.5 mm plus or minus 0.3 mm. The height 232 of the notches 221 as illustrated is on the order of 0.5 mm and similarly the thickness 231 of crossbar 201 and a notch 221 is preferably approximately 2.25 mm. The height 229 of spinal staple 200 is preferably on the order of 16 mm plus or minus 0.3 mm. The distance 233 between adjacent notches 221 is approximately 1.5 mm. As previously mentioned, variations in these design parameters (heights, widths, thicknesses, angles, etc.) that would occur to a person of ordinary skill in the art are contemplated as within the scope of the invention.

With reference to FIGS. 4A–4E, another embodiment of a spinal staple 300 is illustrated. Vertebral interbody staple 300 is generally U-shaped with cross bar 301 between legs 302 and 303. Staple 300 has inner surface 310 and outer surface 320. Leg 302 has a pointed tip 304 and leg 303 has a pointed tip 305 for insertion into the vertebral bodies. It should be understood that tips 304, 305 may have a variety of configurations. The back of staple 300 has a plurality of notches 321 for final seating of the staple into the bone or vertebrae. Notches 321 aid the surgeon in driving in each tine or leg 302, 303 independently as necessary.

To better illustrate the construction of the staple 300, the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. Spinal staple 300 has a center line 315 around which it is symmetrical. An angle 325 subtended by axis 315 and a line extending from the tip 305 of leg 303 preferably defines an angle of 50 degrees. Similarly, the angle 326 is preferably 70 degrees. The width 330 of the staple 300 between tip 304 and tip 305 is preferably 9.5 mm and the greatest width 327 of staple 300 is preferably 17.18 mm. The height 329 of spinal staple 300 is preferably on the order of 10 mm. The distance 333 between adjacent notches 321 is approximately 2 mm. As previously mentioned, variations in these design parameters that would occur to a person of ordinary skill in the art are contemplated as within the scope of the invention.

With reference to FIGS. 5A–5E, another embodiment of the shape-memory alloy staple is shown. The embodiments of the shape-memory alloy staple shown in FIGS. 3–4 are two pronged, whereas the embodiment shown in FIGS. 5A–5E is a four prong staple. Shape-memory alloy staple 400 has four prongs or tines 402, 404, 406, 408 with pointed tips 403, 405, 407, and 409 respectively. The prongs 402, 404, 406, 408 are interconnected by a cross plate 401 which preferably is integrally formed with the prongs. The staple 400 is symmetrical about the imaginary axis 415 which bisects the width of the staple 400. Crossbar or cross plate 401 has a bore 450 defined therein extending between exterior surface 420 and interior surface 410. The bore 450 is defined by a tapered insertion surface 460 adjoining a surface 461 generally parallel to the axis 415. Bore 450 is intended to receive a bone anchor or a fastener such as a screw or a bolt. This fastener may be attached to other fasteners received in the bores of other staples by an artificial strand or adjustable tether such as those previously described in the application entitled "Adjustable Spinal Tether."

To better illustrate the construction of the staple 400, the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. The greatest width 427 of staple 400 is on the order of 19.5 mm plus or minus 0.3 mm. The lesser width 430 separating pointed tips 403 and 407 or 405 and 409 respectively is on the order of 9.5 mm plus or minus 0.3 mm. Preferably bore 450 is countersunk and has a circular cross section defined by surface 461 having a diameter on the order of 6.5 mm. The thickness 431 of crossbar or cross plate 401 is on the order of 2.25 mm. The width 428 of crossbar or cross plate 401 is on the order of 10 mm. The height 429b defined between the pointed tips of the legs of the staple 400 and the arch formed between adjacent legs 402 and 404 or 406 and 408 respectively is approximately 12 mm. The total height 429a from the pointed tips to the top most portion of the outer portion 420 of cross plate 401 is approximately 16 mm plus or minus 0.3 mm. The height 462 of tapered insertion surface 460 along axis 415 parallel to the axis 415 is approximately 1 mm. The width 470 of the arch formed between adjacent legs 406 and 408 or 402 and 404 respectively is approximately 6 mm. The angles 426 subtended by each tip 403, 405, 407, and 409 between inner surface 410 and outer surface 420 is approximately 27 degrees plus or minus 5 degrees. Similarly, the angle 425 subtended between axis 415 and a line tangential to the outer surface 420 at any of the tips is approximately 37 degrees plus or minus 5 degrees. The outer radius 471 of outer surface 420 of cross plate 401 is 20 mm. The outer radius 473 of outer surface 420 at the junction between cross plate 401 and any of the prongs 402, 404, 406, 408 is 4.75 mm. The inner radius 474 of inner surface 410 at the junction between cross plate 401 and any of the prongs 402, 404, 406, 408 is 2.5 mm. The outer radius 476 of the prongs 402, 404, 406, 408 is 16 mm. The inner radius 477 of the prongs 402, 404, 406, 408 is 13.75 mm. As previously mentioned, variations in these design parameters that would occur to a person of ordinary skill in the art are contemplated as within the scope of the invention.

With reference to FIGS. 6A–6E, another embodiment of a shape-memory alloy staple having four prongs is shown. Shape-memory alloy staple 500 has four prongs or tines 502, 504, 506, 508 with pointed tips 503, 505, 507, and 509 respectively. The prongs 502, 504, 506, 508 are interconnected by a cross plate 501 which preferably is integrally formed with the prongs. The staple 500 is symmetrical about the imaginary axis 515 which bisects the width of the staple 500. Cross plate 501 has a bore 550 as defined therein extending between exterior surface 420 and interior surface 510. The bore 550 is defined by a tapered insertion surface 560 adjoining a surface 561 generally parallel to the axis 515. Bore 550 is intended to receive a bone anchor fastener such as a screw or a bolt. Again, as in the just described embodiment, this fastener may be attached to other fasteners received in the bores of other staples by an artificial strand or adjustable tether such as those previously described in the application entitled "Adjustable Spinal Tether."

To better illustrate the construction of the staple 500, the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. The greatest width 527 of staple 500 is on the order of 20.0 mm plus or minus 0.3 mm. The lesser width 530 separating pointed tips 503 and 507 or 505 and 509 respectively is on the order of 9.5 mm. Preferably bore 550 is counter sunk and has a circular cross section defined by surface 561 having a diameter on the order of 6.5 mm. The thickness 531 of crossbar or cross plate 501 is on the order of 2.25 mm. The width 528 of cross plate 501 is on the order of 10 mm. The height 529b defined between the pointed tips of the legs of the staple 500 and the arch formed between adjacent legs 502 and 504 or 506 and 508 respectively is approximately 12 mm. The total height 529a from the pointed tips to the top most portion of the back of the staple as defined by cross plate 501 is approximately 16 mm plus or minus 0.3 mm. The height 562 of tapered insertion surface 560 along axis 515 parallel to the axis 515 is approximately 1 mm. The width 570 of the arch formed between adjacent legs 506 and 508 or 502 and 504 respectively is approximately 6 mm. The angle 525 subtended between axis 515 and a line tangential to the exterior surface 520 at any of the tips is approximately 37 degrees plus or minus 5 degrees. The outer radius 571 of outer surface 520 of cross plate 501 is 25 mm. The outer radius 573 of outer surface 520 at the junction between cross plate 501 and any of the prongs 502, 504, 506, 508 is 4.75 mm. The inner radius 574 of inner surface 510 at the junction between cross plate 501 and any of the prongs 502, 505, 506, 508 is 2 mm. The outer radius 576 of the prongs 502, 504, 506, 508 is 16.75 mm. The inner radius 577 of the prongs 502, 504, 506, 508 is 19 mm. It should be noted that in contrast to radii 476, 477 of the embodiment in FIGS. 5A–5E, the radii 576, 577 are in a different direction. That is to say that the curvature of the prongs of the embodiment of a staple in FIGS. 6A–6E is such that the prongs bend inward toward the imaginary axis 515. Thus giving the prongs of the latter embodiment a wavy shape. As previously mentioned, variations in these design parameters that would occur to a person of ordinary skill in the art are contemplated as within the scope of the invention.

With reference to FIGS. 3D, 4E, 5E and 6E, the deformed martensitic insertion shape of the legs of the staples is shown in phantom. It should be understood that this deformed state may arise from the formation of martensite because of temperature conditions or the formation of stress induced martensite from the application of a force. After the various embodiments of the staples are inserted in their open position, either the stress is released or the staple is heated so that the staple attempts to reform to its closed memorized shape.

Figure 7A:
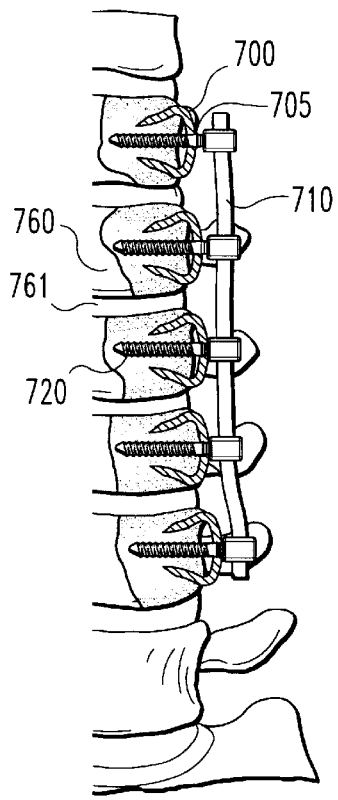
FIG. 7A is a front view of an intrabody staple application for use with bone screws and a single spinal rod for deformity.
Figure 7B:
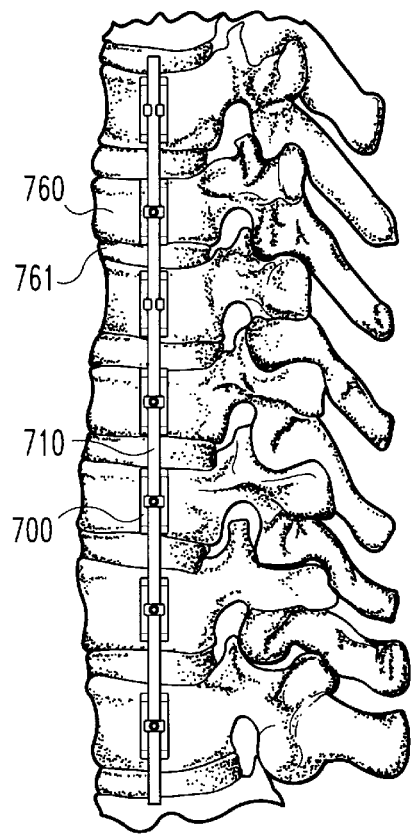
FIG. 7B is a side view of the embodiment of FIG. 7A.
Figure 8:
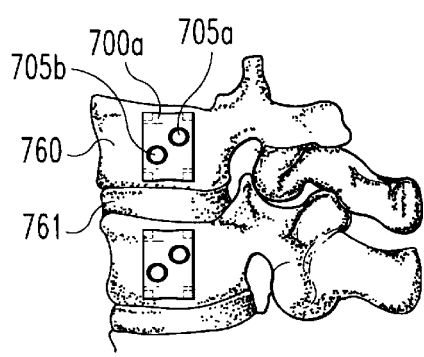
FIG. 8 is another embodiment of a staple for intrabody application with two apertures (permitting the use of dual longitudinal members) in the staple.
Figure 9A:
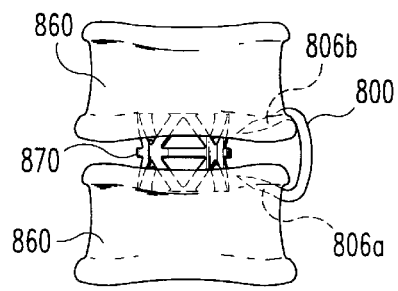
FIG. 9A is a front view of an interbody staple application for use with a graft in interbody fusions.
Figure 9B:
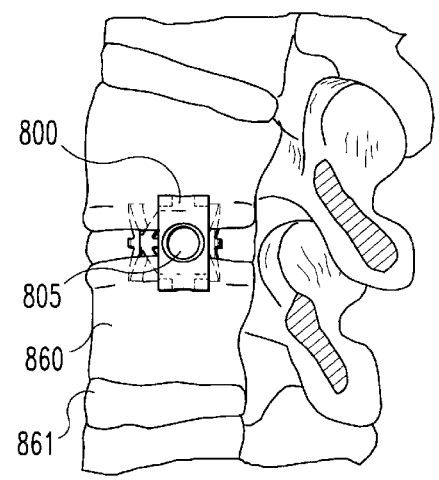
FIG. 9B is a side view of the embodiment of FIG. 9A.

With respect to FIGS. 7 and 8, there are illustrated intrabody staple applications for use with bone screws. In particular, with reference to FIGS. 7A and 7B, there is shown front and side views, respectively, of an intrabody staple application for use with bone screws and a single spinal rod for correction of deformity. In particular, SMA staple 700 is implanted into vertebral bodies 760. Since this is an intrabody application, it is not intended that SMA staple 700 span intervertebral disc 761. SMA staple 700 has an aperture 705 which receives a bone screw 720. A variety of bone screws may be used as bone screw 720, as known to those of ordinary skill in the art, such as the MAS™, VA™ screw, Liberty™ screw, CD Horizon™ screw, etc., etc. These and other bone screws 720 known to those of ordinary skill in the art interconnect with a longitudinal element which in the example illustrated is a rod 710. In the embodiments illustrated in FIGS. 7A and 7B, a single rod is used for the correction of deformity in for example such surgical implantations as the Dwyer technique and others known to those of ordinary skill in the art. The SMA staple 700 shown in the embodiments of FIGS. 7A and 7B could be an altered form of the two-prong embodiments previously disclosed with the addition of an aperture defined therethrough. It should be understood, however, that the four-prong embodiments previously disclosed above in the present patent application may be better suited for use in the intrabody staple applications since the staple is at least in part acting as an anchor.

With reference to FIG. 8 there is illustrated another intrabody staple application. Again, SMA staple 700a is implanted within vertebral body 760. The primary difference being that SMA staple 700a has two apertures, a first aperture 705a, and a second aperture 705b for receiving bone screw 720 (not shown). Again, bone screw 720 may be a variety of bone screws known to those of ordinary skill in the art, such as MAS™, VA™ screw, Liberty™ CD Horizon™, etc., etc. In the intrabody staple application illustrated in FIG. 8, however, the SMA staple 700a has two apertures permitting the use of dual longitudinal elements (such as two rods) for such conditions as tumors and/or trauma to the spine.

With respect to FIGS. 9–12, there is shown a variety of interbody (across disc) SMA staple applications. It should be understood that SMA staple 800 may be either of the two-prong or four-prong embodiments previously discussed in the present patent application. For example, while staple 800 is shown as having two prongs 806a and 806b, it is equally plausible for all of the applications in FIGS. 9–12 that the four-prong version of the SMA staples of the embodiments previously disclosed could instead be used. With respect to FIGS. 9A and 9B, there is shown an interbody application of an SMA staple 800 for use with interbody fusions. In this example, SMA staple 800 has prongs 806a and 806b, each of which is implanted into a different vertebral body 860. Located between vertebral bodies 860 is a graft 870. It should be understood that the graft 870 may be selected from a variety of different grafts. For example, the graft may be bone transplanted from another portion of the patient's body or it may be a commercial implant graft such as PYRAMESH™ and other grafts known to those of ordinary skill in the art. In particular, it should be understood that the illustrations of the application of an SMA staple in an interbody fusion of FIGS. 9A and 9B in conjunction with a graft are equally applicable to the cervical, thoracic, and lumbar regions of the spine.

Figure 10:
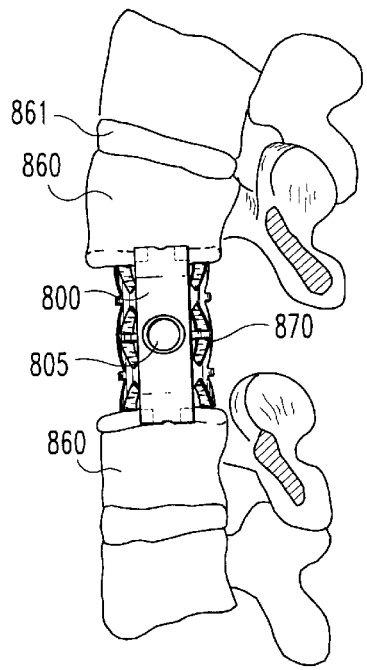
FIG. 10 is an embodiment of a shape memory alloy staple for use after a corpectomy.

With respect to FIG. 10 there is shown an interbody application of SMA staple 800 for use in a corpectomy. The SMA staple 800 spans an excised intervertebral body 860 (not shown as it has been removed) and the prongs (not shown) of SMA staple 800 are implanted into the vertebral bodies 860 that were adjacent the now removed vertebral body. Implanted into the void left by the corpectomy, may be a variety of different grafts 870 such as those discussed above and for example a titanium surgical mesh.

Figure 11A:
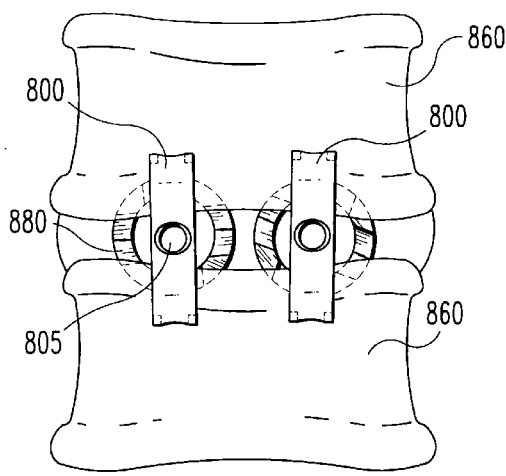
FIG. 11A is a front view of an interbody staple application on the front of the spine for use with cages to prevent cage migration.
Figure 11B:
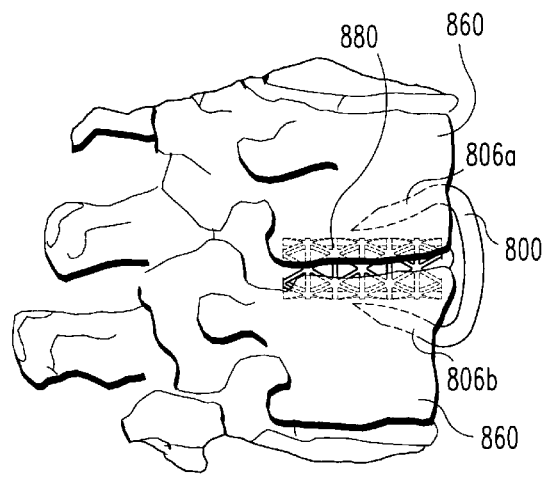
FIG. 11B is a side view of the embodiment of FIG. 11A.

With respect to FIGS. 11A and 11B there are shown front and side views, respectively, of an application of SMA staple 800 to prevent cage migration. In particular, the cages 880 are implanted in the space once occupied by an intervertebral disc surrounded by adjacent vertebral bodies S60. The implanted SMA staple 800, which may include aperture 805, is placed in the front of the spine after the cages 880 have been implanted to prevent the migration or movement of the cages 880.

Figure 12A:
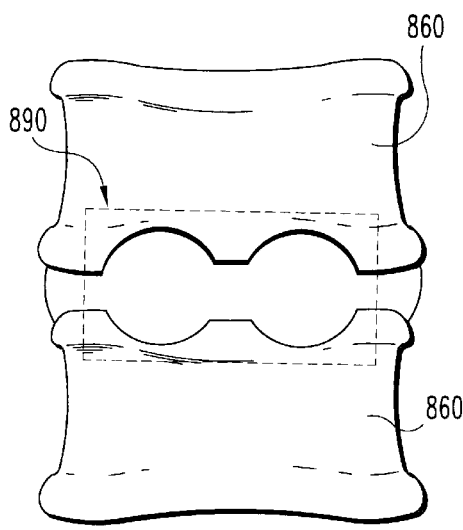
FIG. 12A is a front view of an interbody staple application after the removal of old cages with the area of the vertebral bodies to be reamed out with box and reamers shown in phantom.
Figure 12B:
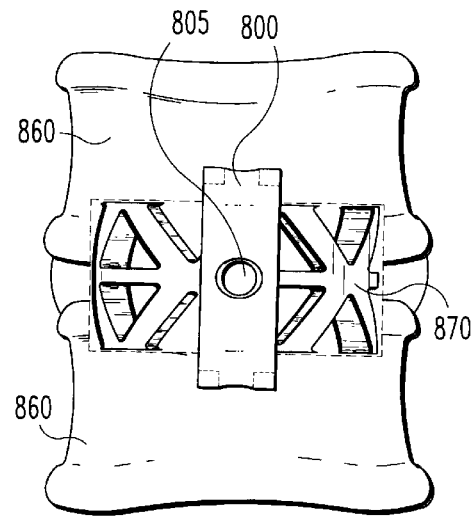
FIG. 12B is the interbody staple application shown in the front of the spine for use after cage revision after reaming with the emplacement of the graft or other implant compressed by a shape memory alloy staple of the present invention.

With respect to FIGS. 12A and 12B, there is illustrated a portion of the procedure in which an SMA staple is used for cage revision. The first step is the removal of the old cages from the location in the void between adjacent vertebral bodies 860. The next step is to ream out the vertebral bodies with box end reamers creating a void generally designated by the rectangular portion 890 in FIG. 12A. After reaming out the vertebral bodies with box end reamers, a surgeon would implant the graft 870 (which may be a femoral ring bone graft or PYRAMESH™ or other grafts known to those of ordinary skill in the art) in the void created by the reaming out of the vertebral bodies 860. Next, the SMA staple 800 is implanted with the prongs (not shown) inserted into the adjacent vertebral bodies 860. The SMA staple 800 will compress the vertebral bodies 860 onto and thus greatly aid retention of the graft 870. With respect to all of the grafts, such as graft 870 which may be made from PYRAMESH™, one example of such a graft is found in U.S. Pat. No. 5,879,556 to Drewry et al. entitled "Device for Supporting Weak Bony Structures" which is herein incorporated by reference. It should be understood, however, that a variety of grafts known to those of ordinary skill in the art are equally aided by the use of SMA staple 800 in a variety of applications.

It was previously mentioned that various problems exist in the prior art. Fusionless tethering addresses several of these problems. For example, curve stabilization with thoracoscopic stapling would subject patients with juvenile scoliosis to fewer and less destructive procedures. Also, while anterior and/or posterior spinal fusion in the skeletally immature patient often results in loss of vertebral body height and girth, thoracoscopic stapling would allow continued growth of the remaining vertebral body. The removal of the staples or other fusionless tethers after correction of the deformity permits further growth, thus minimizing the loss of vertebral body height and girth. Another problem mentioned is that some children, while not currently candidates for a definitive fusion procedure, are likely to need such a procedure in the future. Fusionless tethering of the convex side generally, and vertebral interbody stapling in particular, offers an alternative method of curve stabilization for these children. This method allows such children to continue growth while their curve is restrained from progression.

As has been described with respect to FIGS. 7–12, a number of surgical procedures will benefit by the use of the SMA staple embodiments disclosed in the present application. In particular, as previously discussed with respect to FIGS. 7 and 8, the SMA staple embodiments of the present invention may be used in intrabody staple applications for use with bone screws in both single and double aperture staples for use in the correction of deformity with the single rod (for example, the Dwyer technique) or the use of dual rods for trauma and/or tumors. Additionally, as illustrated further in the applications of FIGS. 9–12, a variety of interbody SMA staple applications which may make use of two prong or four prong SMA staple designs are possible. In brief, these interbody staple applications include use with a graft (in cervical, thoracic, and lumbar regions of the spine), use with titanium surgical mesh or other grafts in corpectomies, use in the front of the spine with cages to prevent cage migration, and use in front of the spine after cage revision. These and other surgical applications known to those of ordinary skill in the art benefit from the improvements disclosed in the present application for various embodiments of SMA spinal staples.

While the invention has been illustrated and described in detail in the drawings and foregoing description, the same is to be considered illustrative and not restrictive in character, it being understood that only the preferred embodiments have been shown and described and that all changes and modifications that come within the spirit of the invention are desired to be protected.

What is claimed:

1. A spinal staple, comprising:
   a cross member defining an opening extending therethrough;
   a first prong extending from a first end portion of said cross member; and
   a second prong extending from a second end portion of said cross member; and
   wherein the staple is at least partially formed of a shape-memory material having a memorized state and a deformed state, said opening having an initial cross section when in said deformed state and a different cross section when in said memorized state.

2. The spinal staple of claim 1, wherein said initial cross section is larger than said different cross section.

3. The spinal staple of claim 1, wherein said opening is generally circular.

4. The spinal staple of claim 1, wherein said initial cross section is sized to receive a portion of a bone anchor; and
   wherein said different cross section is sized to capture said portion of the bone anchor.

5. The spinal staple of claim 1, wherein said first and second prongs are disposed closer to one another in said memorized state than in said deformed state.

6. The spinal staple of claim 1, wherein a pair of said first prongs extends from said first end portion of said cross member; and
   wherein a pair of said second prongs extends from said second end portion of said cross member.

7. A spinal staple, comprising:
   a cross member;
   a first pair of prongs extending from a first end portion of said cross member;
   a second pair of prongs extending from a second end portion of said cross member; and
   wherein the staple is at least partially formed of a shape-memory material having a deformed state and a memorized state, said first and second pairs of prongs being disposed closer to one another in said memorized state than in said deformed state.

8. The spinal staple of claim 7, said cross member includes an opening extending therethrough, said opening having an initial cross section when in said deformed state and a different cross section when in said memorized state.

9. The spinal staple of claim 8, wherein said initial cross section is sized to receive a portion of a bone anchor; and
   wherein said different cross section is sized to capture said portion of the bone anchor.

10. The spinal staple of claim 7, wherein each prong of said first and second pairs of prongs includes a distal portion, said distal portions of said first and second pairs of prongs being disposed closer to one another in said memorized state than in said deformed state.

11. The spinal staple of claim 7, wherein each prong of said first and second pairs of prongs includes a distal portion defining a pointed tip to aid in insertion of said first and second pairs of prongs into bone.

12. The spinal staple of claim 7, wherein said first and second pairs of prongs are substantially parallel in said deformed state.

13. The spinal staple of claim 7, wherein said first and second pairs of prongs are angled toward one another when transformed toward said memorized state.

14. The spinal staple of claim 7, wherein said cross member includes an inwardly facing concave surface.

15. The spinal staple of claim 7, wherein said first pair of prongs are interconnected by a first arched portion, and wherein said second pair of prongs are interconnected by a second arched portion.

16. The spinal staple of claim 7, wherein each prong of said first and second pairs of prongs is curved.

17. The spinal staple of claim 16, wherein each prong of said first and second pairs of prongs includes an inwardly facing concave surface.

18. The spinal staple of claim 16, wherein each prong of said first and second pairs of prongs includes an inwardly facing convex surface.

19. The spinal staple of claim 7, wherein transformation from said deformed state toward said memorized state causes a dynamic compression.

20. A spinal staple, comprising:

a cross member;

a first pair of prongs extending from a first end portion of said cross member;

a second pair of prongs extending from a second end portion of said cross member; and wherein the staple is at least partially formed of a shape-memory material having a deformed state and a memorized state, said first and second pairs of prongs being disposed closer to one another in said memorized state than in said deformed state, wherein transformation from said deformed state toward said memorized state occurs without a corresponding change in temperature.

21. An apparatus for treatment of the spine, comprising:

at least two staples, each staple being at least partially formed of a shape-memory material having a deformed state and a memorized state, each staple comprising:

a cross member defining an opening extending therethrough;

a first prong extending from a first end portion of said cross member; and a second prong extending from a second end portion of said cross member, wherein said first and second prongs are disposed closer to one another in said memorized state than in said deformed state;

at least two bone anchors, a portion of each bone anchor extending through said opening in a corresponding one of said staples; and a longitudinal element interconnecting said at least two bone anchors.

22. The apparatus of claim 21, wherein said opening has an initial cross section when in said deformed state and a different cross section when in said memorized state.

23. The apparatus of claim 22, wherein said initial cross section is sized to receive said portion of the bone anchor; and wherein said different cross section is sized to capture said portion of the bone anchor.

24. The apparatus of claim 21, wherein a pair of said first prongs extends from said first end portion of said cross member; and wherein a pair of said second prongs extends from said second end portion of said cross member.

25. The apparatus of claim 21, wherein said at least two bone anchors are capable of being engaged to respective ones of said vertebral bodies.

26. The apparatus of claim 21, wherein said at least two bone anchors are bone screws.

27. The apparatus of claim 21, wherein said longitudinal element is a spinal rod.

28. An apparatus for treatment of the spine, comprising:

an implant capable of being disposed between adjacent vertebral bodies; and a staple at least partially formed of a shape-memory material having a deformed state and a memorized state, said staple comprising:

a cross member;

a first prong extending from a first end portion of said cross member and capable of being engaged to one of said vertebral bodies; and a second prong extending from a second end portion of said cross member and capable of being engaged to another of said vertebral bodies; and wherein said first and second prongs are disposed closer to one another in said memorized state than in said deformed state; and wherein transformation from said deformed state toward said memorized state compresses said vertebral bodies against said implant.

29. The apparatus of claim 28, wherein said staple is capable of retaining said implant between said adjacent vertebral bodies.

30. The apparatus of claim 29, wherein said staple inhibits movement of said implant relative to said adjacent vertebral bodies.

31. The apparatus of claim 28, wherein said implant is a graft.

32. The apparatus of claim 28, wherein said implant is a fusion device.

33. The apparatus of claim 28, wherein a pair of said first prongs extends from said first end portion of said cross member; and wherein a pair of said second prongs extends from said second end portion of said cross member.

34. The apparatus of claim 28, wherein said first and second prongs are substantially parallel in said deformed state and are angled toward one another in said memorized state.

* * * * *